United States Patent [19]

Krantz et al.

[11] Patent Number: 4,661,510

[45] Date of Patent: Apr. 28, 1987

[54] α-ALLENIC-α-AMINO ACIDS AS ENZYME INHIBITORS

[75] Inventors: Alexander Krantz, Toronto; Arlindo L. Castelhano, Mississauga, both of Canada

[73] Assignee: Syntex (U.S.A.) Inc., Palo Alto, Calif.

[21] Appl. No.: 790,000

[22] Filed: Oct. 21, 1985

Related U.S. Application Data

[63] Continuation-in-part of Ser. No. 524,476, Aug. 17, 1983, abandoned.

[51] Int. Cl.[4] .................. A61K 31/415; C07D 233/64
[52] U.S. Cl. .................................. 514/400; 562/557; 562/561; 514/419; 562/567; 562/571; 514/510; 562/574; 564/164; 514/538; 564/197; 564/198; 514/542; 514/547; 514/549; 514/562; 514/563; 514/564; 514/565; 514/566; 548/104; 548/344; 548/495; 560/9; 560/10; 560/34; 560/39; 560/40; 560/41; 560/153; 560/169; 560/170; 560/171; 560/172; 562/426; 562/443; 562/444; 562/445; 562/446; 562/450; 562/556

[58] Field of Search ............... 562/574, 426, 557, 556, 562/567, 444, 443, 450, 561, 446, 445, 571; 548/344, 495, 104; 560/9, 10, 34, 39, 40, 41, 153, 169-172; 564/164, 197, 198; 514/400, 419, 510, 538, 542, 547, 549, 562-566

[56] References Cited

U.S. PATENT DOCUMENTS

| | | | |
|---|---|---|---|
| 3,946,060 | 3/1976 | Metcalf et al. | 514/63 |
| 3,959,356 | 5/1976 | Metcalf et al. | 260/501.11 X |
| 3,960,927 | 6/1976 | Metcalf et al. | 260/501.11 X |
| 4,103,089 | 7/1978 | Metcalf et al. | 548/344 |
| 4,147,873 | 4/1979 | Metcalf et al. | 546/221 |
| 4,275,220 | 6/1981 | Patchett et al. | 560/35 |
| 4,325,877 | 4/1982 | Metcalf et al. | 560/105 X |
| 4,347,375 | 8/1982 | Patchett et al. | 548/344 |

OTHER PUBLICATIONS

Black, D., et al., J. Chem. Soc. (C), pp. 283-287 (1968).

Primary Examiner—Richard A. Schwartz
Attorney, Agent, or Firm—Liza K. Toth; Tom M. Moran

[57] ABSTRACT

Novel α-allenic-α-amino acids which are enzyme inhibitors of the suicide or $k_{cat}$ type are disclosed herein.

29 Claims, No Drawings

α-ALLENIC-α-AMINO ACIDS AS ENZYME INHIBITORS

This application is a continuation-in-part of U.S. application Ser. No. 524,476, filed Aug. 17, 1983, now abandoned.

BACKGROUND OF THE INVENTION

1. Field of the Invention

This invention relates to α-allenic-α-amino acids which are useful as enzyme inhibitors of the suicide or $k_{cat}$ type.

2. Background Art

Suicide enzyme inhibitors are substances bearing a latent reactive group that is unmasked by the target enzyme itself and, upon being unmasked, reacts with the enzyme in an irreversible manner, thus inactivating it.

A number of enzyme inhibitors of the suicide type are known in the art, see for example the reviews by Walsh, Horizons in Biochem., Biophys., 3, 36–81 (1977) and Jung, M. J., and J. Koch-weser, "Molecular Basis of Drug Action," Singer and Ondarza, Ed., 135–150 (1981), Elsevier North Holland Inc.

The most common prosthetic group of target decarboxylases is normally pyridoxal-5'-phosphate. However, two enzymes are known in which the prosthetic group is a pyruvoyl residue attached to the protein chain: mammalian S-adenosyl L-methionine-decarboxylase and bacterial histidine decarboxylase. The mechanism of action of the pyridoxal-dependent enzymes can be summarized as follows: the α-amino acid enters the enzyme's active site and forms a Schiff-base with the aldehyde function of the cofactor already bound to the enzyme. Carbon dioxide is then eliminated, generating a negative charge on the α-carbon which can be delocalized over the whole pyridine nucleus of the cofactor. Protonation usually takes place on the α-carbon atom giving, after hydrolysis, the corresponding amine and pyridoxal phosphate. It has been suggested that in pyridoxal catalysis, the α-carbon bond to be broken must lie in a plane perpendicular to the plane of the cofactor-amine system in order to minimize the energy of the transition state. One role of the enzyme is, therefore, to freeze the conformation of the amino acid-pyridoxal adduct in this special arrangement.

The process of decarboxylation and protonation appears to be stereo-specific and occurs with retention of configuration. The mechanism of decarboxylation catalyzed by the pyruvoyl-dependent enzymes is presumably similar, the carbonyl group of the pyruvate replacing the aldehyde function of pyridoxal-5'-phosphate.

Various types of chemical modifications of the substrate likely to generate enzyme-activated irreversible inhibitors have been synthesized and investigated. For example, replacement of the α-hydrogen by a vinyl or ethynyl group can generate an α, β-unsaturated imine, a good Michael acceptor. A number of α-vinyl or α-ethynyl substituted amino acids had been prepared and tested as suicide inhibitors of decarboxylase enzymes. This concept has also been tested by incorporation of the double bond directly into the amino acid chain rather than as a replacement of the α hydrogen. It has been found that β, γ-dehydroornithine is a very potent competitive inhibitor of ornithine decarboxylase. See Relyea, N and R. R. Rando, Biochem. Biophys. Res. Comm., 67:292–402 (1975). Also it has been found that α-methyl-trans-dehydroglutamic acid irreversibly inhibits rat brain glutamate decarboxylase, Crystal, E., et al, J. Neurochem., 32:1501–1507 (1977).

The amine analogs of the α-halomethyl substituted and β, γ-unsaturated amino acids have also been tested as decarboxylase enzyme inhibitors. Not unsurprisingly, several compounds from both of these classifications have been found to be active in several systems. For example (R) 4-amino-hex-5-ynoic acid has been found to inhibit bacterial and mammalian glutamate decarboxylase, Jung, M. J., et al, Biochem., 17:2628–2632 (1978). The compound (−)-5-hexyne-1,4-diamine has been found to be a potent time-dependent inhibitor of rat liver and rat prostate ornithine decarboxylase. See Metcalf, B. W., et al, J. Amer. Chem. Soc., 100:2551–2553 (1979), α-ethynyl- and α-vinyl-dopamine cause a slow-time dependent inactivation of aromatic amino acid decarboxylase. See Maycock, A. L., et al, "Drug Action and Design: Mechanism-Based Enzyme Inhibitors, "Elsevier, North Holland, pp. 115–129.

It is the object of this invention to provide a group of novel α-allenic substituted amino acids wherein the β, γ-unsaturation provides a reactive site which is capable of undergoing an irreversible action with the enzyme target thus abolishing decarboxylase activity.

SUMMARY OF THE INVENTION

One embodiment of this invention is directed to a new class of $k_{cat}$ or suicide enzyme inhibitors. The inhibitors are α-allenic substituted α-amino acids of the formula:

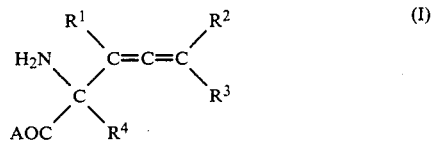

(I)

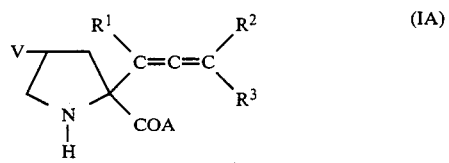

(IA)

or a pharmaceutically acceptable salt thereof wherein:

$R^1$, $R^2$ and $R^3$ are selected from the group consisting of: hydrogen; alkyl; trifluoromethyl; phenyl; and phenylalkyl of 7 to 9 carbons where the ring is substituted with halo, halo alkyl, alkyl, hydroxy, alkoxy or amino; wherein at least two of $R^1$, $R^2$ and $R^3$ are hydrogen or alkyl; and wherein at least one of $R^2$ and $R^3$ is hydrogen when $R^4$ is hydrogen;

$R^4$ is selected from the group consisting of: hydrogen; lower akyl; —(CHR)$_m$XR′ wherein m is 1 or 2 and X is oxygen or sulfur and R and R′ are independently hydrogen or methyl; —(CH$_2$)$_n$—COY wherein n is 1 or 2 and Y is hydroxy or amino; —(CH$_2$)$_o$NHC(NH$_2$)(NH) wherein O is 2, 3 or 4; —(CH$_2$)$_p$—NH$_2$ wherein p is 2, 3, 4 or 5; a radical of the formula

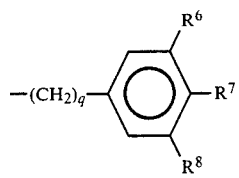

wherein q is 1 or 2 and $R^6$, $R^7$ and $R^8$ are independently hydrogen or hydroxy; and a radical of the formula

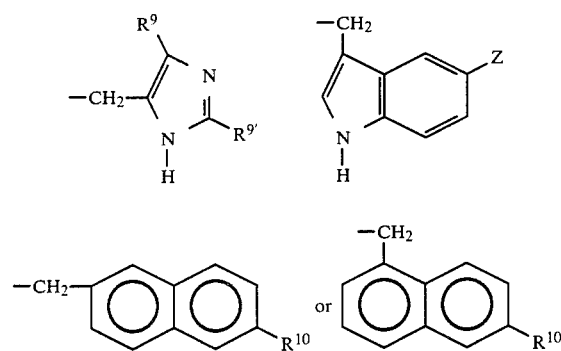

wherein $R^9$ and $R^{9'}$ are independently hydrogen or trifluoromethyl, $R^{10}$ is hydrogen, hydroxy or methoxy, and Z is hydrogen or hydroxy;

V is selected from the group consisting of: hydrogen; hydroxy; $NH_2$; α-aminocarbonyl; and a natural α-amino acid; and A is selected from the group consisting of: —OH; —OS wherein S is a cationic portion of a pharmaceutically acceptable salt; —OE wherein E is alkyl of 1 to 22 carbon atoms or arylalkyl of 7 to 10 carbon atoms; amino; mono-alkylamino; and di-alkyl amino.

A second aspect of this invention relates to a method for inhibiting amino acid decarboxylase enzyme activity. This method comprises administering a therapeutically effective amount of a compound of Formula (I) or (IA) to a mammal.

A further aspect of this invention relates to a method for treating fungal infections. This method comprises administering a therapeutically effective amount of a compound of Formula (I) or (IA) to a mammal.

In yet another aspect, this invention relates to a pharmaceutical composition comprising a therapeutically effective amount of a compound according to formula (I) or (IA) in admixture with a pharmaceutically acceptable excipient.

DETAILED DESCRIPTION OF THE PREFERRED EMBODIMENTS

The preferred compounds of this invention are those wherein: $R^1$, $R^2$ and $R^3$ are independently hydrogen, methyl, ethyl, trifluoromethyl or benzyl; and $R^4$ is selected from the group consisting of: hydrogen; methyl; —(CH$_2$)$_3$—NH$_2$; —(CH$_2$)$_4$NH$_2$; —(CH$_2$)$_2$—COY wherein Y is hydroxy or amino; a radical of the formula

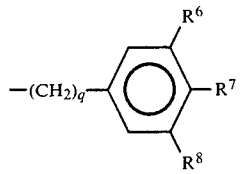

where q is 1 or 2 and $R^6$, $R^7$ and $R^8$ are independently hydrogen or hydroxy; and a radical of the formula wherein $R^9$ and $R^{9'}$ are independently hydrogen, alkyl of 1 to 4 carbons, halo or trifluoromethyl, $R^{10}$ is hydrogen, hydroxy or methoxy and Z is hydrogen or hydroxy.

More preferred are those compounds of formula (I) wherein $R^1$, $R^2$ and $R^3$ are hydrogen and wherein $R^4$ is defined according to the previous paragraph; or wherein $R^1$ and $R^4$ are hydrogen, and one of $R^2$ and $R^3$ is hydrogen and the other is methyl.

The most preferred compounds are:
2-amino-3-methylpenta-3,4-dienoic acid;
2-amino-2-(imidazol-4-ylmethyl)penta-3,4-dienoic acid;
2-amino-2-(2-carboxyethyl)penta-3,4-dienoic acid;
2-amino-2-(3-amino-n-propyl)penta-3,4-dienoic acid;
2-amino-2-(3-hydroxybenzyl)penta-3,4-dienoic acid;
2-amino-2-(4-hydroxybenzyl)penta-3,4-dienoic acid;
2-amino-2-(3,4-dihydroxybenzyl)penta-3,4-dienoic acid;
2-aminopenta-3,4-dienoic acid;
2-amino-2-(3-hydroxybenzyl)penta-3,4-dienoic acid;
2-amino-2-(3,4-dihydroxybenzyl)penta-3,4-dienoic acid;
2-amino-2-benzylpenta-3,4-dienoic acid;
2-amino-2-(4-amino-n-butyl)penta-3,4-dienoic acid;
2-amino-2-methylpenta-3,4-dienoic acid;
2-amino-2-(5-hydroxyindol-3-ylmethyl)penta-3,4-dienoic acid;
2-amino-2-(3-hydroxybenzyl)hexa-3,4-dienoic acid;
2-amino-2-benzylhexa-3,4-dienoic acid; and
2-amino-2-(3-amino-n-propyl)penta-3,4-dienoic acid.

Other compounds of the invention include 2-amino-2-(β-naphthylmethyl)penta-3,4-dienoic acid and 2-amino-2-benzyl-3-methylpenta-3,4-dienoic acid.

Definitions

"Alkyl" refers to a group consisting of hydrogen and carbon which is fully saturated and may be straight or branched, and, unless otherwise qualified, refers to a radical having 1 to 6 carbon atoms. The phrase is specifically exemplified by such radicals as methyl, ethyl, propyl, isopropyl, n-butyl, t-butyl, n-pentyl, n-hexyl or the like. Similarly, the term alkoxy is generally limited to those alkoxy radicals of 1 to 6 carbon atoms unless otherwise specified. Examples are methoxy, ethoxy, propyloxy, n-butyloxy, pentyloxy, hexyloxy or the like. In addition, when reference is made to alkyl amino or di-alkyl amino, the alkyl group is understood to be coextensive with the phase alkyl.

The term "halo" refers to fluoro, chloro, bromo or iodo. Halo alkyl encompasses an alkyl radical substituted on the terminal carbon by one, two or three halo atoms. Examples are fluoromethyl, difluoromethyl, trifluoromethyl, chloromethyl, dichloromethyl, trichloromethyl, 2,2-dichloroethane and the like.

"Natural α-amino acids" refer to naturally occurring α-amino acids such as alanine, valine, leucine, isoleucine, proline, glycine, serine, threonine, cysteine, tyrosine, tryptophan, aspartic acid, glutamic acid, histidine, asparagine, phenylalanine, arginine, lysine, methionine and glutamine. "Unnatural α-amino acids" are those that are either commercially available or readily synthesized by one of ordinary skill in the art.

"Phenylalkyl of 7 to 9 carbons" encompasses benzyl, phenethyl, phenylpropyl and phenylbutyl or isomers of the latter two radicals. The phenyl group may be substituted with one or more substituents as recited herein above. Any combination of substituents may be present where more than one substituent is substituted on the ring. If more than one substituent is present, it is preferred that they all be the same, such as a trihalo substituent pattern.

"DOPA" represents 3,4-dihydroxyphenylalanine.

In the compounds of Formula (IA), when V is α-aminocarbonyl, that group may be any α-amino acid safe for mammalian or avian consumption.

Pharmaceutically acceptable non-toxic salts are salts which retain the biological activity of the parent compound, which do not render the compound deleterious, and which are not themselves harmful.

Salts of the free acid may be derived from inorganic bases. Acceptable salts include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, tromethamine, dicyclohexylamine, choline and caffeine.

Acid addition salts may be prepared from the amine. These salts may be derived from inorganic or organic acids. Examples of inorganic acids are hydrochloric acid, nitric acid, hydrobromic acid, sulfuric acid or phosphoric acid. Examples of organic acids are acetic acid, propanoic acid, glycolic acid, lactic acid, pyruvic acid, oxalic acid, malonic acid, succinic acid, maleic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The compounds of Formula (I) and (IA) in free base form may be converted to the acid addition salts by treating with a stoichiometric excess of the appropriate organic or inorganic acid, such as, for example, phosphoric, pyruvic, hydrochloric or sulfuric acid and the like. Typically, the free base is dissolved in a polar organic solvent such as ethanol or methanol, and the acid added thereto. The temperature is maintained between about 0° C. and 100° C. The resulting acid addition salt precipitates spontaneously or may be brought out of solution with a less polar solvent.

The acid addition salts of the compounds of Formula (I) and (IA) may be decomposed to the corresponding free base by treating with a stoichiometric excess of a suitable base, such as potassium carbonate or sodium hydroxide, typically in the presence of aqueous solvent, and at a temperature of between about 0° C. and 100° C. The free base form is isolated by conventional means, such as extraction with an organic solvent.

Salts of the compounds of Formula (I) and (IA) may be interchanged by taking advantage of differential solubilities of the salts, volatilities or acidities of the acids, or by treating with the appropriately loaded ion exchange resin. For example, the interchange is effected by the reaction of a salt of the compounds of Formula (I) and (IA) with a slight stoichiometric excess of an acid of a lower pKa than the acid component of the starting salt. This conversion is carried out at a temperature between about 0° C. and the boiling point of the solvent being used as the medium for the procedure.

The pharmaceutically acceptable non-toxic salt derivatives of the compounds of the invention are prepared by treating the free acids with an appropriate amount of pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, manganous hydroxide, aluminum hydroxide, ferric hydroxide, manganic hydroxide, isopropylamine, trimethylamine, diethylamine, triethylamine, tripropylamine, ethanolamine, 2-dimethylaminoethanol, 2-diethylaminoethanol, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. The reaction is conducted in water, alone or in combination with an inert, water-miscible organic solvent, at a temperature of from about 0° C. to about 100° C., preferably at room temperature. Typical inert, water-miscible organic solvents include methanol, ethanol, isopropanol, butanol, acetone, dioxane or tetrahydrofuran. The molar ratio of compounds of the invention to base used are chosen to provide the ratio desired for any particular salt. For preparing, for example, the calcium salts or magnesium salts the free acid starting material of Formula (I) can be treated with at least one-half molar equivalent of pharmaceutically acceptable base to yield a neutral salt. When the aluminum salts of the compounds of Formula (I) are prepared, at least one-third molar equivalent of the pharmaceutically acceptable base are employed if a neutral salt product is desired.

The salt derivatives of the compounds of formula (I) and (IA) can be reconverted to their respective free acids by acidifying said salts with an acid, preferably an inorganic acid, e.g., hydrochloric acid, sulfuric acid, and the like, at temperature of from about 0° C. to about 50° C., preferably at room temperature.

The esters of Formula (I) and (IA) are prepared by esterifying the corresponding free acids with an alcohol reagent corresponding to the desired ester, e.g., an alkanol having up to 12 carbon atoms or with glycerol which is already esterified at two hydroxyls to other suitable acids. This reaction is conducted in the presence of a strong acid, such as boron trifluoride, hydrogen chloride, sulfuric acid, p-toluenesulfonic acid, and the like. If the alcohol reagent used in the esterification is a liquid at the reaction temperature, the alcohol reagent can be the reaction solvent. Optionally, the reaction can be carried out in an inert organic solvent in which the free acids and the alcohol reagent are soluble, such as a hydrocarbon solvent, e.g., hexane, isooctane, decane, cyclohexane, benzene, toluene, xylene, a halogenated hydrocarbon solvent, e.g., methylene chloride, chloroform, dichloroethane; or an ether solvent, e.g., diethyl ether, dibutyl ether dioxane, tetrahydrofuran, and the like. In the case where the alcohol reagent is a solid, the reaction preferably is conducted in a non-aqueous liquid inert organic solvent. The reaction is conducted at from about 0° C. to the reflux temperature of the reaction mixture, preferably using hydrogen chloride at a temperature of from 15° C. to about 35° C.

The product is isolated by conventional means such as diluting the reaction mixture with water, extracting the resulting aqueous mixture with a water-immiscible inert organic solvent, such as diethyl ether, benzene, methylene chloride, and the like, combining the extracts, washing the extracts with water to neutrality and then evaporating under reduced pressure.

Typical esters are those ester derivatives prepared from methyl alcohol, ethyl alcohol, propyl alcohol, isopropyl alcohol, butyl alcohol, 2-butyl alcohol, 2-pentyl alcohol, isopentyl alcohol, 2-hexyl alcohol, and the like.

Alternatively, the alkyl esters can be prepared by transesterification, according to methods known in the art. It is preferred in preparing the esters via transesterification to go from a lower ester to a higher ester, e.g., from the methyl ester, for example, to the isoamyl ester, for example. However, by using a substantial excess of a lower alcohol, a higher ester can be transesterified to a lower ester; thus, for example, by using a substantial excess of ethanol, the hexyl ester is converted by the transesterification to the ethyl ester.

The compounds of the present invention may be prepared in either optically active form or as racemic mixtures. Unless otherwise specified, the compounds described herein are all in the racemic form. However, the scope of the subject invention herein is not to be considered limited to the racemic forms, but to encompass the individual optical isomers of the compounds.

If desired, the compounds herein may be resolved into their optical antipodes by conventional resolution means, for example by separation (e.g. fractional crystallization) of the diastereomeric salts formed by the reaction of these compounds with optically active acids. Exemplary of such optically active acids are the optically active forms of camphor-10-sulfonic acid, 2-bromo-camphor-10-sulfonic acid, camphoric acid, menthoxyacetic acid, tartaric acid, maleic acid, diacetyltartaric acid, pyrrolidine-5-carboxylic acid and the like. The separated pure diastereomeric salts may then be cleaved by standard means to afford the respective optical isomers of the compounds of formula (I) or (IA).

Utility

Many of the compounds of Formula (I), especially where $R^1$ and $R^2$ and $R^3$ are hydrogen and A is OH, are irreversible enzyme inactivators that have general utility as titrating reagents for the identification and quantification of enzyme activities both in vivo and in vitro. Such tools are useful for identifying abnormal levels of enzyme activity in disease states.

Compounds of Formula (I) wherein $R^2$, $R^3$ and $R^4$ are hydrogen possess anti-microbial activity. For example, the compound of Formula (I) wherein $R^2$, $R^3$ and $R^4$ are hydrogen and $R^1$ is methyl was active in vitro against a spectrum of dermatophytes.

Additionally, the compounds of Formula (I), especially the following such compounds:

2-amino-2-benzylpenta-3,4-dienoic acid;
2-amino-2-(3,4-dihydroxybenzyl)penta-3,4-dienoic acid;
2-amino-2-(3-hydroxybenzyl)penta-3,4-dienoic acid;
2-amino-2-(4-hydroxybenzyl)penta-3,4-dienoic acid;
2-amino-2-(3-hydroxybenzyl)hexa-3,4-dienoic acid; and
2-amino-2-benzylhexa-3,4-dienoic acid are irreversible inactivators of aromatic amino acid decarboxylases such as mammalian DOPA decarboxylase from porcine kidney, bacterial tyrosine decarboxylase from Streptococcus faecallis and phenylalanine decarboxylase from Streptococcus faecallis.

The selective inhibition of DOPA Decarboxylase in the peripheral organs can be used in combination with L-DOPA to potentiate DOPA behavioural effects in the treatment of Parkinson's disease. Both 2-amino-2-(3,4-dihydroxybenzyl)penta-3,4-dienoic acid and 2-amino-2-(3-hydroxybenzyl)penta-3,4-dienoic acid potentiate DOPA behaviors in mice at does of 3 to 30 mg/kg, intraperitoneum (i.p.), or 30 to 150 mg/kg, subcutaneous (s.c.), (see Example 25).

Further, the compounds of Formula (I), and particularly the compound 2-amino-2-(3-amino-n-propyl)penta-3,4-dienoic acid, are irreversible inactivators of mammalian ornithine decarboxylase from rat liver or bacterial ornithine decarboxylase from E. Coli.. Ornithine decarboxylase catalyzes the rate determining step in the formation of putrescine and the polyamines spermidine and spermine. This enzyme has been identified as a key regulatory protein in cellular growth, differentiation and replication.

Ornithine decarboxylase inhibitors have a spectrum of therapeutic utilities, including antitumor, antiviral, and antibacterial and antitrypanosomal activities.

For example, oral administration of Ornithine Decarboxylase inactivators suppresses B16 melanoma development in mice. Total or near total suppression of tumor growth has been observed in mice receiving combination therapy of an ornithine decarboxylase inactivator and interferon. [See: Science 219, 851 (1983)].

Additionally, increased polyamine synthesis has been associated with replication of cytomegaloma virus (CMV), respiratory syncytical virus and, to a lesser degree, herpes simplex virus. Production of these viruses is markedly inhibited in cells depleted of polyamines by treatment with ornithine decarboxylase inactivators. [See: J. Virol. 50, 145 (1984); Biochem. Biophys. Res. Commun. 86, 312 (1979); Med. Biology 59, 428 (1981)].

Moreover, bacterial growth is inhibited by restriction of polyamine biosynthesis. [See: Biochem. J. 208, 435 (1982)].

Finally, therapeutic utility of Ornithine Decarboxylase inactivators in trypanosomal infections is derived from rapid depletion of spermidine, a polyamine essential for survival of parasitic protozoa. [See: Mechanism of Drug Action, p. 159, Academic Press, 1983)].

The compound 2-amino-2-(imidazol-ylmethyl)-penta-3,4-dienoic acid was designed as specific inactivator of pyridoxal phosphate dependent Histidine Decarboxylase. Histidine decarboxylation is the only known biosynthetic route to histamine production. The inhibition of histidine decarboxylase can alleviate the histamine mediated symptomology in human disease states, and thus inactivators of this enzyme have utility as anti-histamics.

Administration and Dosage

Administration of the active compounds and salts described herein can be via any of the accepted modes of administration for agents which inhibit decarboxylase enzyme activity. These methods include oral, parenteral and otherwise systemic or aerosol forms.

Depending on the intended mode of administration, the compositions used may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula (I) or the pharmaceutically acceptable salts thereof and, in addition, may include other medicinal agents, pharmaceutical agents, carriers, adjuvants, etc.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

Of course, the dosage will vary depending upon the type and severity of the affliction, the condition and identity of the host, the mode of administration, and the judgment of the prescribing physician. As a general rule, when the compounds of the present invention are administered systemically for inhibiting decarboxylase activity in mammals, a therapeutically effective dosage will be in the range of from about 0.5 μg to about 20 μg per kg of body weight, and preferably from about 5 mg to about 10 mg per kg of body weight. When the compounds are used for treatment of fungal infections, they are preferably applied topically. A therapeutically effective topical dosage will generally comprise approximately 2% active ingredient in the formulation.

PREPARATIONS AND EXAMPLES

The preferred method for preparing the compounds of this invention is first to block the reactive functional groups of an α-amino acid other than the carboxyl group, then to esterify the acid function with an α-acetylenic alcohol, and then to effect a Claisen rearrangement which gives an oxazolone ring structure which is then opened by alcoholysis. The amino acid is obtained by hydrolysis.

Because of the variety of reactive functional groups present in α-amino acids, the foregoing synthetic outline may have to be modified in terms of the type of protecting groups employed and the sequence of steps employed to make the compounds of this invention. Though variations will be needed, the general scheme for making these compounds is set forth in Reaction Scheme I.

REACTION SCHEME I

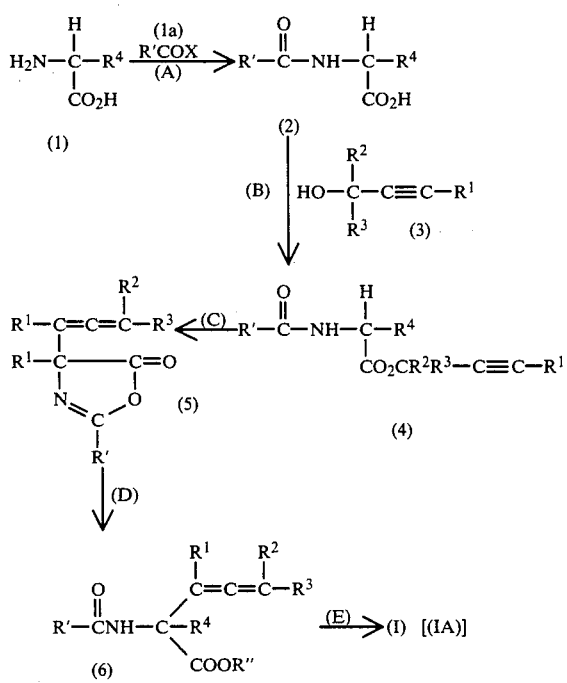

wherein $R^1$, $R^2$, $R^3$, $R^4$ are defined above, X is a halogen atom or a carboxyl activating group as known in the art of peptide synthesis, R' is a blocking group described below, and R'' is an ester forming group.

The starting materials of Formulas (1), (1a) and (3) can be commercially obtained or can readily be made by one of ordinary skill in the art. Specifically, materials of Formula (1) are obtained, for example, from Aldrich Chemical Co., Inc., Sigma Chemical Company, Chemical Dynamics Corporation, Bachem Inc., etc., when $R^4$ is a natural amino acid side chain, such as: methyl, benzyl, 3-hydroxybenzyl, 3,4-dihydroxybenzyl, 3-amino-n-propyl, imidazol-4-ylmethyl, carboxyethyl, indol-3-ylmethyl, 5-hydroxy-indol-3-ylmethyl, etc.; or are made by Strecker's Amino Acid Synthesis or by any of the several methods of amino acid synthesis known in art when $R^4$ is an unnatural amino acid side chain. Similarly, materials of Formula (1a) comprising any of the blocking groups listed below are commercially available from Aldrich Chemical Co., Inc., Chemical Dynamics, etc. The acetylenic alcohols of Formula (3) are commercially available from Aldrich Chemical Co., Inc., K and K Laboratories, Pfaltz and Bauer Inc., Wiley Organics, or Farchan Laboratories Inc. when $R^1$, $R^2$, and $R^3$ are hydrogen or alkyl. Alternatively, the remaining alcohols can readily be made by reacting the appropriate metal acetylide such as lithium acetylide with the appropriate alkyl or aryl aldehyde or ketone. The foregoing acetylene, aldehyde and ketone precursors are all readily available.

In step (A), an α-amino acid is reacted with a reagent which will block the reactive functional groups on the acid side chain other than the acid functionality itself. Suitable blocking groups are t-butyloxycarbonyl (Boc), benzyloxycarbonyl, biphenylisopropoxycarbonyl, t-amyloxycarbonyl, isobornyloxycarbonyl, o-nitrophenylsulfenyl, 2-cyano-t-butyloxycarbonyl, 9-fluorenylmethyloxycarbonyl and the like. The ω-functionalities of arginine may be protected with nitro, p-toluenesulfonyl, 4-methoxybenzenesulfonyl, benzyloxycarbonyl, Boc and adamantyloxycarbonyl.

The preferred method for protecting reactive side chain functionalities herein comprises treating the α-amino acid with benzoyl chloride under the conditions of Schotten and Bauman. See *Chemistry of the Amino Acids*, Ed. Greenstein and Winitz, John Wiley & Sons, Vol. 2, 1961. The amide is formed by adding about 1.1 equivalents of benzoyl chloride per side chain functional group dropwise to the amino acid in a basic aqueous solution at a reduced temperature, for example between about $-10°$ and $+10°$ C. A pH of about 9 to about 10 is maintained by addition of dilute base. It is preferred to use 1.0M sodium hydroxide as the reactant and for maintaining the pH. The reaction is effected in about 1 to about 4 hours, after which the pH is lowered to about 3 with mineral acid. The resulting precipitate is collected and further purified by conventional means. When the α-amino acid is one such as m- and p-tyrosine, DOPA, lysine, ornithine, 5-hydroxytryptophan, or the like, the additional functionalities are protected by adjusting the number of equivalents in the foregoing procedure.

In step (B), the preparation of acetylenic esters is carried out according to the method of Hassner [A. Hassner and V. Alexanian, Tetrahedron letters, 46, 4475, (1978)]. The protected amino acid is taken up in a dry, polar aprotic solvent and treated at room temperature with 1.0 to 1.15 equivalents each of dicyclohexyldiimide (DCC) or 1-(dimethylaminopropyl)-3-ethylcarbodiimide.HCl, the appropriate acetylenic alcohol and 0.1–0.2 equivalents of N,N-4-dimethylaminopyridine (DMAP). The reaction is run at room temperature for about 6 to 16 hours after which the ester is purified by crystallization, chromatography or other conventional means.

The acetylenic esters of the α-amino protected histidine are prepared by refluxing 2 to 5 equivalents of the appropriate acetylenic alcohol and between 1–1.4 equivalents of p-toluenesulfonic acid in a non-polar solvent such as benzene in a Dean-Stark apparatus until a stoichiometric amount of water is produced. The solvent and excess reagents are then removed in vacuo and the resulting residue crystallized from a polar solvent as the p-toluenesulfonic acid salt.

In step (C), the Claisen rearrangement is effected using the method of W. Steglich et al., *Ang. Chem. Int. Ed.*, 14, 1, 58, (1975) or W. Steglich et al., ibid, 16, 6 394 (1977). The acetylenic ester is taken up in a dry, polar solvent such as a acetonitrile at about room temperature under an inert atmosphere such as argon and treated with about 3 to about 3.5 equivalents of triethylamine, about 2.0 to about 2.5 equivalents of carbon tetrachloride and about 2 equivalents of triphenyl phosphine. Trichloromethyl chloroformate may be used in place of carbon tetrachloride and triphenyl phosphine. The rearrangement is complete in about 4 to about 24 hours.

Rearrangement of amino acids having a second protected amine function, such as ornithine, lysine, or histidine, require a doubling of the reagents.

In step (D), opening of the oxazolone ring is done by methanolysis or by some other simple alcohol. The alcohol is added directly to the reaction pot after the rearrangement is determined to be complete and the solution is left stand at room temperature overnight. This procedure effects ring opening, giving the allenic methyl ester or similar ester depending on the alcohol used.

Hydrolysis of histidine compounds is accomplished using a dilute solution of a strong mineral acid at an elevated temperature. For example, the oxazolone is dissolved in an approximately 10 to approximately 30% solution of hydrochloric acid, preferably 20%, and heated in a range of between about 60° to about 90° C., and preferably about 80° C. for several hours.

Other amides may be hydrolyzed by treating them with about 3 equivalents of triethyloxonium tetrafluoroborate at room temperature for up to 5 days. The solvent is then removed under vacuum and the residue treated with diluted 5% aqueous acetic acid in a compatible organic solvent such as tetrahydrofuran overnight at room temperature. The methyl ester is saponified using a dilute solution of a strong base in an organic alcohol, for example 1.0N NaOH in methanol (1:2) to give a compound of Formula (I) or (IA).

An alternative method for producing the compounds of Formula (5) is to effect a Claisen rearrangement of the protected α-acetylenic esters employing Ireland's enolate method. See R. E. Ireland, et al., *J.A.C.S.*, 98:10, 2868, (1976). The reaction is carried out as follows: A protected α-acetylenic ester dissolved in a dry, organic solvent such as tetrahydrofuran is added with stirring under argon to a premade solution of lithium diisopropylamide (LDA) at $-78°$ C. generated from diisopropylamide and N-butyl lithium. About 20 to 40 minutes after the addition, chlorotrimethylsilane is added in one portion and the solution allowed to warm to room temperature over about 1 hour. The reaction mixture is then heated to between about 40° and about 65° C. (preferably about 55° C.) for about 4 to 7 hours (preferably about 5 hours) cooled, and treated with a dilute solution of acid such as acetic acid (about 10%) and methanol to hydrolyze the intermediate trimethylsilyl ester. The protecting groups are then hydrolyzed to generate the desired α-allenic-α-amino acids.

A further understanding of the invention may be obtained from the following non-limiting Examples.

EXAMPLE 1

2-(Benzoylamino)-3-(4-benzoyloxyphenyl)propionic acid

Tyrosine (5.0 g) was dissolved in 30 ml of 2N sodium hydroxide at 0° C. To this solution, 7 ml of benzoyl chloride was added portion-wise. The pH of the solution was constantly monitored and kept at approximately 10. After approximately 4 hours with constant pH the solution was acidified to pH 3.0 with concentrated hydrochloric acid, yielding a precipitate which was left at 0° C. for 2 hours. The precipitate was filtered, boiled over carbon tetrachloride and recrystallized from ethanol-water (1:1).

Proceeding in the same manner, but substituting the appropriate amino acid for tyrosine, and adjusting the acylating reagents according to the number of functional groups to be reacted, the following exemplary compounds may be prepared:

2-(benzoylamino)butan-1,4-dioic acid;
2-(benzoylamino)pentan-1,5-dioic acid;
2-(benzoylamino)butanoic acid;
2-(benzoylamino)propanoic acid;
2-(benzoylamino)acetic acid;
2-(benzoylamino)-3-imidazol-4-ylpropanoic acid;
2-(benzoylamino)-3-methylpentanoic acid;
2-(benzoylamino)-4-methylpentanoic acid;
2-(benzoylamino)-4-methylthiobutanoic acid;
2-(benzoylamino)-3-phenylpropanoic acid;
2-(benzoylamino)-3-methylpentanoic acid;
2-(benzoylamino)-3-(naphth-2-yl)propanoic acid;
2-(benzoylamino)-3-(naphth-1-yl)propanoic acid;
2-(benzoylamino)-3-(6-methoxynaphthyl-2-yl)propanoic acid; and
2-(benzoylamino)-3-(6-methoxynaphthyl-2-yl)propanoic acid.

EXAMPLE 2

2-(Benzoylamino)-3-(3,4-dibenzoyloxyphenyl)-propanoic acid

In 25 ml of 0.1N NaOH, was dissolved 2 g of 2-amino-3-(3,4-dihydroxyphenyl)propanoic acid. To the resulting solution, 3.8 ml of benzoyl chloride was added dropwise. The reaction mixture was maintained at a temperature of 0° C. for the duration of the reaction. The pH was maintained in a range of approximately by the addition of 0.2N NaOH. After about 3 hours, the reaction mixture was acidified with concentrated hydrochloric acid. The precipitate was removed by filtration and taken up in boiling carbon tetrachloride. The precipitate was then crystallized to yield a 2-(benzoylamino)-3-(3,4-dibenzoyloxyphenyl)propanoic acid.

Proceeding in a similar manner, but substituting for 2-amino-3-(3,4-dihydroxyphenyl)propanoic acid another α-amino acid and adjusting the amount of benzoyl chloride to equal appropriate equivalents of hydroxyl, amine, or thiol groups to be protected, for that set forth in the preceding paragraph, there may be prepared, for example, the following compounds:

2,6-di(benzoylamino)-5-benzoyloxyhexanoic acid;
2-(benzoylamino)-4-(benzoylcarbamoyl)butanoic acid;
2-(benzoylamino)-3-benzoylthiopropanoic acid;
2-(benzoylamino)-5-(benzoylcarbamoyl)pentanoic acid;
2,6-di(benzoylamino)-4-benzoyloxyhexanoic acid;
2,6-di(benzoylamino)hexanoic acid;
2,5-di(benzoylamino)pentanoic acid;
2-(benzoylamino)-3-benzoyloxypropanoic acid;
2-(benzoylamino)-3-benzoyloxybutanioc acid;
2-(benzoylamino)-3-(indol-3-yl)propanoic acid;
2-(benzoylamino)-3-(5-hydroxyindol-3-yl)propanoic acid;
2-(benzoylamino)-3-(3-benzoyloxyphenyl)propanoic acid; and
2-(benzoylamino)-3-(3,4-dibenzoyloxyphenyl)-propanoic acid.

EXAMPLE 3

Propargyl 2-(benzoylamino)-3-(4-benzoyloxyphenyl)propanoate 9.3 g of 2-(benzoylamino)-3-(4-benzoyloxyphenyl)-propanoic acid was dissolved in 50 ml of dry methylene chloride which was maintained at 0° C. in an ice bath. Propargyl alcohol (4.2 ml) was added, followed by 9.8 g of DCC and 0.6 g of DMAP. The reaction mixture was warmed to room temperature. After 6 hours, the reaction mixture was filtered into a separatory funnel and washed with 5% acetic acid (2×), water (1×), and 5% sodium bicarbonate (1×). The methylene chloride was dried over magnesium sulphate and evaporated. The residue was recrystallized from methylene chloride:ether (1:2) to give propargyl 2-(benzoylamino)-3-(4-benzoyloxyphenyl)propanoate ester.

Proceeding in a similar manner, but substituting for 2-(benzoylamino)-3-(4-benzoyloxyphenyl)propanoic acid, and using propargyl alcohol or another appropriate acetylenic alcohol, the mono-acids prepared by Example 1 and 2 may be converted to the corresponding ester, to obtain, for example:

propargyl 2-(benzoylamino)-3-benzoylthiopropanoate;
propargyl 2,6-di(benzoylamino)hexanoate;
propargyl 2,5-di(benzoylamino)pentanoate;
propargyl 2-(benzoylamino)-3-benzoyloxypropanoate;
propargyl 2-(benzoylamino)-3-benzoyloxybutanoate;
propargyl 2-(benzoylamino)-3-(indol-3-yl)propanoate;
propargyl 2-(benzoylamino)-3-(5-hydroxyindol-3-yl)-propanoate;
propargyl 2-(benzoylamino)-3-(3-benzoloxyphenyl)-propanoate;
propargyl 2-(benzoylamino)-3-(3,4-dibenzolyoxyphenyl)propanoate;
dipropargyl 2-(benzoylamino)butan-1,4-dionate;
dipropargyl 2-(benzoylamino)pentan-1,5-dionate;
propargyl 2-(benzoylamino)acetate;
propargyl 2-(benzoylamino)-3-imidazol-4-yl propanoate;
propargyl 2-(benzoylamino)-3-phenylpropanoate;
propargyl 2-(benzoylamino)-3-naphth-2-yl)propanoate;
but-2-yn-1-yl 2-(benzoylamino)-3-phenylpropanoate;
but-3-yn-2-yl 2-(benzoylamino)-3-(3-benzoloxyphenyl)propanoate;
but-2-yn-1-yl 2-(benzoylamino)-3-(3-benzoloxyphenyl)propanoate; and
but-3-yn-2-yl 2-(benzoylamino)-3-phenylpropanoate.

EXAMPLE 4

Methyl 2-(benzoylamino)-2-(4-benzyoloxybenzyl)-3,4-pentadienoate

A 4.7 g of aliquot of propargyl 2-(benzoylamino)-3-phenylpropanoate was placed in a reaction flask which was then flushed with argon. Dry acetonitrile (from phosphorus pentoxide) was added to the flask after which 4.6 ml of triethylamine was added followed by 2.4 ml of carbon tetrachloride and 5.76 g of triphenylphosphine with stirring and under argon. The reaction mixture was maintained at room temperature, the progress of the reaction being followed by monitoring the appearance of the 1820–1830 $cm^{-1}$ band of the oxazolone ring and the appearance of the 1950–1960 cm$^{-1}$ band of the allene group. After about 4.5 hours at room temperature, 10 ml of dry methanol was added to the reaction flask and the mixture maintained at room temperature overnight by which time the 1820–1830 cm$^{-1}$ band of the oxazolone ring had disappeared.

The mixture was evaporated to dryness and the residue taken up in toluene and chromatographed on silica, eluting with ethyl acetate petroleum ether (10% step increments from petroleum ether to ethyl acetate). The ester-containing fractions were concentrated under reduced pressure to give the title product.

Proceeding in the same manner but substituting for propargyl 2-(benzoylamino)-3-phenylpropanoate, other mono-ester compounds prepared as per Example 3 are converted to their corresponding α-allenic acid methyl ester.

EXAMPLE 5

2-Amino-2-(4-hydroxybenzyl)penta-3,4-dienoic acid

To 1.33 g of 2-(benzoylamino)-2-(4-benzoyloxybenzyl)penta-3,4-dienoic acid methyl ester in 5 ml of dry methylene chloride was added 9 ml of 1.0M solution of Meerwein's reagent triethyloxonium tetrafluoroborate at room temperature with stirring and under argon. The reaction was left at room temperature for five (5) days with stirring under argon. The reaction mixture was then concentrated under vacuum and the residue was taken in 10 ml of tetrahydrofuran and 5 ml of 5% acetic acid and left overnight at room temperature with stirring under argon. The resulting reaction mixture was then diluted with 50 ml of ether and extracted 3 times with 2% hydrochloric acid (15 ml). The aqueous fractions were combined and the pH adjusted to 7.5 in a two-phase system containing methylene chloride. The aqueous extraction was further extracted with 3×30 ml of methylene chloride. The organic fractions were pooled, dried over anhydrous magnesium sulfate, and concentrated to give a residue which was then taken up in 15 ml of methanol and 10 ml of a 2.0N sodium hydroxide solution and left stirring overnight under argon. This mixture was then diluted with 30 ml of ether and extracted with water (3×15 ml). The pH of the aqueous layer was adjusted to 2.5 and the sample desalted by passing the the aqueous solution through an ion exchange column (BioRad Ag 50w×8), eluting with 20% pyridine-water. Appropriate eluant fractions were concentrated under vacuum and the residue taken up in water, the pH adjusted to the pI of tyrosine and absolute ethyl alcohol added. Resulting crystals of the title compound were collected and characterized as follows: mp 270°–275° C. (dec), IR (KBr); 1958 cm$^{-1}$ (C=C=C), $^1$HNMR; (delta D$_2$O); 3.05 (AB, 2H, —CH2—), 5.0 (d, 2H, CH$_2$=C), 5.5 ppm (dd, 1H, CH=C), MH+ 220.

Proceeding in a similar manner but substituting for 2-(benzoylamino)-2-(4-benzoyloxybenzyl)penta-3,4-dienoic acid methyl ester, the esters of Example 4, there may be prepared, for example, the following compounds:

2-Amino-2-(3-hydroxybenzyl)penta-3,4-dienoic acid: mp 242°–246° C. (dec), IR(KBr): 1958 cm$^{-1}$ (C=C=C), $^1$H NMR*: (delta D$_2$O): 3.25 (AB, 2H, CH$_2$—), 5.15 (2H, m, CH$_2$=C), 5.7 ppm (1H, m, HC=C).
*Only pertinent resonances shown.

2-Amino-2-benzylpenta-3,4-dienoic acid:
mp 210°–220° C. (dec), IR (KBr): 1962 cm$^{-1}$ (C=C=C), $^1$H NMR*: (delta D$_2$O): 3.15 (AB, 2H, —CH$_2$—), 5.0 (d, 2H, CH$_2$=C), 5.55 ppm (dd, 1H, CH=C), $^{13}$C NMR: (delta D$_2$O): 208.6 ppm (C=C=C), MH+204.
*Only pertinent resonances shown.

2-Amino-2-benzylhexa-3,4-dienoic acid:
Two diastereoisomers were obtained and partially separated by HPLC RP-18 (5% MeOH water, pH 4.5 acetate citrate (2:1) buffer). The more polar isomer: mp 220° C. (dec), IR (KBr): 1962 cm$^{-1}$ (C=C=C), $^1$H NMR: (delta D$_2$O): 1.7 (dd, 3H, CH$_3$—), 5.6 ppm (m, 2H, HC=C). $^{13}$C NMR: (delta D$_2$O): 205.5 ppm (C=C=C). The less polar somer: mp 195° C. (dec), IR (KBr): 1960 cm$^{-1}$(C=C=C), $^1$H NMR: (delta D$_2$O): 1.65 (dd, 3H, CH$_3$), 5.6 ppm (m, 2H, CH=C), $^{13}$C NMR: (delta D$_2$O): 205.2 ppm (C=C=C). In the same manner, 2-amino-2-(3-hydroxybenzyl)hexa-3,4-dienoic acid was prepared.

2-Amino-2-benzyl-3-methylpenta-3,4-dienoic acid:
mp 213°–214° C. (dec), IR (KBr): 1955 cm$^{-1}$(C=C=C), $^1$H NMR: (delta D$_2$O): 1.75 (t, 3H, CH$_3$), 3.17 (AB, 2H, CH$_2$—), 4.92 ppm (q, 2H, CH$_2$=C), $^{13}$C NMR: (delta D$_2$O): 208.7 ppm (C=C=C).

2-Amino-2-(3,4-dihydroxybenzyl)-penta-3,4-dienoic acid:
mp 230°–240° C. (dec), IR (KBr): 1955 cm$^{-1}$ (C=C=C), $^1$H NMR: (delta D$_2$O): 3.25 (AB, 2H, —CH$_2$), 5.3 (d, 2H, CH$_2$=C), 5.8 ppm (dd, 1H, CH=C), MH+236.

2-Amino-2-(β-naphthylmethyl)-penta-3,4-dienoic acid:
$^1$H NMR: (delta D$_2$O): 3.5 (AB, 2H, —CH$_2$—), 5.2 (d, 2H, CH$_2$=C), 5.8 (dd, 1H, CH=), 7.3–9.0 ppm (m, 7H, naphthyl).

4-Amino-4-carboxyl-hepta-5,6-dienoic acid hydrochloride:
mp 171° C. (dec), IR (KBr): 1960 cm$^{-1}$ (C=C=C), $^1$H NMR: (delta D$_2$O): 2.45 (m, 4H, —CH$_2$—), 5.25 (d, 2H, H$_2$C=C), 5.65 ppm (dd, 1H, HC=O), $^{13}$C NMR: (delta D$_2$O): 209.0 ppm (C=C=C), MH+186.

EXAMPLE 6

2-(Benzoylamino)penta-1,5-dioic acid dipropargyl ester

Propargyl alcohol (4.6 ml) was added to dry methylene chloride. 5.0 g of N-benzoylglutamic acid was added with stirring followed by 9.0 g of DCC and 0.5 g of DMAP at 0° C. The reaction mixture was warmed to room temperature and the reaction allowed to proceed overnight. The reaction mixture was filtered into a separatory funnel and washed with 5% acetic acid (2×), water (1×), and 5% sodium bicarbonate (1×). The methylene chloride was dried over magnesium sulphate and evaporated. The residue was taken up in ethyl acetate, filtered and concentrated under reduced pressure to give the title product. Other diacids may be converted to the same or other acetylenic diester in the same manner.

EXAMPLE 7

2-Amino-2-methylpenta-3,4-dienoic acid

A solution of 0.7 g of N$^2$-phthaloylalanine propargyl ester in 4 ml of tetrahydrofuran was added with stirring under argon to a premade solution of lithium diisopropylamide (LDA) (2.5 equivalent) at −78° C. The LDA was generated by adding a 1.6M solution of n-butyl lithium to a solution of diisopropylamine in tetrahydrofuran at 0° C. under argon with stirring. This solution was cooled to −78° C. before addition of the propargyl ester. About 30 minutes after addition of the propargyl ester, the reaction was quenched with chlorotrimethylsilane (0.85 ml) and the solution brought to room temperature for one hour. The reaction mixture was then heated to 55° C. for 5 hours, cooled and treated with 10 ml of 10% acetic acid in methanol to hydrolyze the trimethylsilyl ester. The reaction mixture was then diluted with ether and extracted with a 2% NaOH solution, 3×20 ml. The hydroxide solution leads also to the hydrolysis of the trimethylsilyl group of the intermediate 2-(phthaloylamino)-2-methyl-3-trimethylsilylpenta-3,4-dienoic acid. The combined aqueous extracts were acidified to pH 3 in a two-phase system containing dichloromethane, and the aqueous portion further extracted with dichloromethane. Pooled organic fractions were washed with water, brine, dried over magnesium sulfate and concentrated to give the 2-(phthaloylamino)-2-methylpenta-3,4-dienoic acid. This compound was taken up in 10% aqueous HCl and heated at 70° C. for 2 hours, cooled and passed through an ion-exchange column, eluted with water and 20% pyridine-water to give, upon concentration of the appropriate fractions, the title compound.

EXAMPLE 8

Propargyl 4-(benzoylamino)-4-carboxyhepta-5,6-dienoate DCHA salt

To a flask flushed with argon was added 3.19 g of 2-(benzoylamino)penta-1,5-dioic acid dipropargyl ester followed by 25 ml of dry acetonitrile. Triethylamine (3.64 g) was added followed by 2.14 ml of carbon tetrachloride and 5.1 g of triphenylphosphine with stirring and under argon. The progress of the reaction, carried out at room temperature, was monitored by IR, the reaction being complete overnight. 15 ml of 1N NaOH was added, the reaction solution diluted with diethyl ether and extracted with 5% sodium bicarbonate. The aqueous extract was washed with ether (2×), acidified to pH 3.0, and extracted with ethyl acetate. The ethyl acetate fractions were dried over anhydrous magnesium sulfate and concentrated. To the concentrate was added 1.92 ml of dicyclohexylamine (DCHA) to give the title compound as the DHCA salt, mp 154°–156° C. (dec).

EXAMPLE 9

Propargyl 4-(benzoylamino)-4-carbomethoxyhepta-5-6-dienoate

The DCHA salt of propargyl 4-(benzoylamino)-4-carboxyhepta-5,6-dienoate from Example 6 (3.10 g) was partitioned between ethyl acetate and 5% NaHSO$_4$. Two additional NaHSO$_4$ washes were performed, followed by a saturated sodium chloride wash. The ethyl acetate was dried over sodium sulfate and evaporated to dryness. To the residue was added 50 ml of methylene chloride, 1.31 g of DCC, B 0.07 g of DMAP and 0.85 ml of methanol. After 7 hours at room temperature, 1 ml of triethylamine was added to the reaction pot to cause the methanolysis of some oxazolone which also formed. The reaction mixture was left to stand at room temperature overnight, filtered into a separatory funnel and washed twice with 5% acetic acid, water (1×), and sodium bicarbonate (1×). The organic layer was dried with sodium sulfate and evaporated to dryness to give the title compound.

EXAMPLE 10

Propargyl 4-amino-4-carbomethoxyhepta-5,6-dienoate

Propargyl 2-(benzoylamino)-4-carbomethoxyhepta-5,6-dienoate, 1.47 g, was dissolved in 12 ml of dry methylene chloride to which was added 12.9 ml of triethyloxonium tetrafluoroborate with stirring under argon. Dry conditions were carefully maintained. After being stirred for five (5) days, the reaction solution was taken to dryness and then further dried in vacuo. The residue was taken up in 50 ml of tetrahydrofuran/25 ml 10% acetic acid and stirred overnight under argon, partitioned between diethyl ether and 5% HCl and extracted with 5% HCl (4×). The combined extract was placed on an ion-exchange column (BioRad Ag 50×8) and eluted with 1.7M solution of ammonium hydroxide. Appropriate aliquots were combined and taken to dryness in vacuo to give the title compound and methyl 2-amino-4-carbomethoxyhepta-,6-dienoate.

EXAMPLE 11

4-Amino-4-carboxyhepta-5,6-dienoic acid hydrochloride salt

The hydrolysis of propargyl 4-amino-4-carbomethoxyhepta-5,6-dienoate was carried out by dissolving 360 mg of the diester in 10% HCl and heating the solution to 65°–70° C. for about 22 hours. When cooled, the reaction mixture was placed directly on an ion-exchange column (BioRad Ag 50×8) washed with water, and eluted with a 1.7M ammonium hydroxide solution. The ammonium hydroxide fractions were pooled and concentrated to give the free acid of the title compound which was purified further by passing an aqueous solution of the pyrrolidone through a short column of RP-18 material. Upon concentration of the eluant, a residue was obtained which was taken in a dilute HCl solution of pH 3.2. On evaporation to dryness, the title compound was obtained.

EXAMPLE 12

Propargyl 2-(benzoylamino)-3-(indol-3-yl)propionate 2-(benzoylamino)-3-(indol-3-yl)propanoic acid (1.9 g) was dissolved in 75 ml of dry methylene chloride (from phosphorous pentoxide). The solution was cooled to 0° C. in an ice bath and 0.72 ml of propargyl alcohol was added along with 1.39 g of DCC followed by 0.07 g DMAP. The reaction mixture was warmed to room temperature and maintained there for 16 hours. The solution was filtered into a separatory funnel, washed with 5% acetic acid (2×), water (1×) and 5% solution bicarbonate (1×). The separated methylene chloride layer was then dried over magnesium sulfate and evaporated to dryness. The residue was redissolved in ethyl acetate, filtered and the filtrate evaporated to dryness. The orangish residue was dried in vacuo to give propargyl 2-(benzoylamino)-3-(indol-3-yl)propionate.

EXAMPLE 13

Propargyl 2-(benzoylamino)-3-(N$^{in}$-tosylindol-3-yl)-propanoate

Following the method of Fujimo (Chem. Pharm. Bull., 30, 2825, 1982), a 1.61 g amount of propargyl 2-(benzoylamino)-3-(indol-3-yl)propionate was dissolved in 25 ml of methylene chloride to which was added 15 mg of cetyltrimethylammonium chloride followed by 470 mg of pulverized sodium hydroxide. A solution of 1.34 g tosyl chloride in 10 ml of methylene chloride was then added over about 30 minutes. After an additional 30 minutes at room temperature, 24 ml of 10% hydrochloric acid was added with cooling. The organic layer was then washed with water (2×), dried over magnesium sulfate and evaporated to dryness. The resulting residue was passed through a silica gel column (gradient elution, 10% step down from petroleum ether to ethyl acetate). The appropriate fraction were combined and the solvent was evaporated to give the title compound.

EXAMPLE 14

Methyl 2-(benzoylamino)-2-($N^{in}$-tosylindol-3-ylmethyl)-penta-3,4-dienoic acid A 1.38 aliquot of propargyl 2-(benzoylamino)-3-($N^{in}$-tosylindol-3-yl)propionate was placed in a reaction flask which was then flushed with argon. Acetonitrile (20 ml) was added with stirring and under argon followed by 1.04 ml of triethylamine, 0.60 ml of carbon tetrachloride and 1.45 g of triphenylphosphine. Four hours after addition of the triphenylphosphine, 10 ml of methanol was added and the mixture left standing at room temperature overnight. Completion of the reaction was confirmed by disappearance of the 1820 cm$^{-1}$ absorption band. The reaction mixture was then concentrated and run through a silica gel column eluting with ethyl acetate/petroleum ether (10% step down from petroleum ether to ethyl acetate). The ester-containing fractions were combined and the solvent evaporated to give the title compound. IR (neat): 3400, 1960, 1740, 1660 cm$^{-1}$. 'H NMR ($\delta$CDCl$_3$): 2.35 (s, 3H, PhCH$_3$), 3.8 (3H, 3H, OCH$_3$), 4.95 (m, 2H, C=C=CH$_2$), 5.7 (m, 1H, HC=C=C), 6.9 (br s, 1H, NH), 7.0–8.0 ppm (m, 14H, Ph, —NHC=C).

EXAMPLE 15

Propargyl 2-(benzoylamino)-3-(imidazol-4-yl)propionate 5 gm of 2-(benzoylamino)-3-(imidazol-4-yl)propanoic acid in 100 ml of benzene, 5 ml of propargyl alcohol, and 5.22 gm of p-toluenesulfonic acid.H$_2$O was heated at reflux with the azeotropic removal of water by means of a Dean-Stark apparatus. After approximately 2 days of refluxing and the stoichiometric amount of water was produced, the reaction mixture was cooled, and a precipitate, the p-toluenesulfonic acid salt of the title compound was filtered out. The salt was taken up in water, the pH adjusted to 7.5 with 1.0N NaOH in a two phase system of water-dichloromethane. The layers were separated and the aqueous portion extracted 3×30 ml of CH$_2$Cl$_2$. The organic fractions were pooled, dried over anhydrous magnesium sulfate, and concentrated in vacuo to give the title compound.

EXAMPLE 16

Propargyl 2-(benzoylamino)-3-($N^{im}$-benzoylimidazol-4-yl)propanoate

Following the procedure of Beyerman (Recueil, 91), 246, 1972), 1.1 gm of propargyl 2-(benzoylamino)-3-(imidazol-4-yl)propionate was taken up in 30 ml of dry tetrahydrofuran with stirring under argon, 0.8 ml of dicyclohexylamine followed by 0.5 ml of benzoyl chloride were added at room temperature. After 2 hours a white precipitate formed. The precipitate was filtered and the tetrahydrofuran filtrate concentrated in vacuo to yield the product as an oil.

EXAMPLE 17

2-(benzoylamino)-2-($N^{im}$-benzoylimidazol-4-ylmethyl)-penta-3,4-dienoic acid

Propargyl 2-(benzoylamino)-3-($N^{im}$-benzoylimidazol-4-yl)propanoate (6.8 g) was treated with 30 ml of dry acetonitrile to which was added 14.2 ml of triethylamine, 8.2 ml of carbon tetrachloride and 17.8 g of triphenylphosphine with stirring and under argon at 20° C. The reaction mixture was allowed to stand at room temperature for 24 hours and then concentrated in vacuo. The residue was then taken up in 20 ml of 10% HCl and 100 ml of tetrahydrofuran with stirring for 24 hours to hydrolyze the oxazolone and $N^{im}$-benzoyl groups. 100 ml of ethyl acetate were then added to the reaction mixture, and the aqueous portion separated. The organic fraction was extracted 3×30 ml of 10% HCl, the aqueous portion pooled and a pH gradient performed (formate-ammonium formate buffers, BioRad Ag 50×8). The desired fractions were pooled, and desalted with 20% pyridine-water. On concentration the title compound, contaminated with about 10–20% of 2-(benzoylamino)-histidine, was obtained.

EXAMPLE 18

2-Amino-2-(imidazol-4-ylmethyl)-penta-3,4-dienoic acid 2.0 g of 2-(benzoylamino)-2-(imidazol-4-ylmethyl)-penta-3,4-dienoic acid was taken in 20 ml of 20% HCl and heated at 80° C. for 48 hours. The solution was cooled, diluted with 20 ml of water and washed with methylene chloride 3×40 ml. The aqueous phase was adjusted to pH 7.0, cooled to 0° C. and an excess of sodium borohydride added. After two hours at 0° C., the pH was adjusted to 2.0 and the solution introduced onto an ion-exchange chromatography (BioRad Ag 50×8 column), and eluted with 0.3M ammonium acetate buffer pH 4.5–8.0. Fractions between pH 6.5–8.0 were pooled and desalted with 20% pyridine-water. Concentration of the pyridine-water fractions gave an oil which upon fractional crystallization gave the title compound.

EXAMPLE 19

3-(1,2-propadien-1-yl)-3-(benzoylamino)piperidin-2-one

An 11.04 g aliquot of 2,5-di(benzoylamino)ornithine propargyl ester was added to 80 ml of dry acetonitrile, 21.97 ml of triethylamine, 12.48 carbon tetrachloride and 30.69 g of triphenylphosphine. After about 2 hours at room temperature, 50 ml of methanol were added and the solution left at room temperature overnight. The reaction mixture was concentrated in vacuo, and to this residue was added 80 ml of tetrahydrofuran and 40 ml of 10% acetic acid and stirring. After 24 hours at room temperature, the reaction mixture was partitioned between ethyl acetate and 10% HCl. The organic layer was extracted several times with 10% HCl after which the combined aqueous fractions were washed exhaustively with methylene chloride. The pH of the aqueous portion was adjusted to 10 with concentrated sodium hydroxide to induce lactam formation. On cooling, a precipitate formed which was filtered and recrystallized from methanol-ethyl acetate to give the title compound, mp 203°–204° C.

EXAMPLE 20

3-(1,2-Propadien-1-yl)-3-aminopiperidin-2-one

The compound of Example 18 (2.32 g) was introduced into a reaction flash which was then flushed with argon. Dry methylene chloride (45 ml) was added under argon, then 54.40 of triethyloxonium tetrafluoroborate with stirring. The flask was kept at room temperature for 6 days, after which the reaction contents were concentrated in vacuo. A solution of 80 ml tetrahydrofuran and 40 ml of 10% acetic acid were added under argon with stirring at room temperature and the reaction mixture left overnight. It was then partitioned between ethyl acetate-5% HCl and the organic fraction extracted 4×75 ml with 5% HCl. The combined extracts were introduced in an ion-exchange column (BioRad Ag 50×8), washed with water, a 1.7M solution of ammonium hydroxide and then a concentrated ammonium hydroxide solution to elute the title compound. The eluant was dried in vacuo to give the title compound.

This procedure gives predominantly the title compound and a minor amount of 5-amino-2-(1,2-propadien-1-yl)-2-(benzoylamino)pentanoic acid.

EXAMPLE 21

2,5-Diamino-2-(1,2-propadien-1-yl)-pentanoic acid hydrochloride 0.88 g of 3-amino-3-(1,2-propadien-1-yl)piperidin-2-one was taken in 25 ml of 10% HCl and heated to 70° C. overnight. The reaction mixture was then cooled, and introduced in an ion-exchange column, eluting with water, 20% pyridine-water, and finally a 1.7M ammonium hydroxide solution. Pooling the latter fractions and concentrating gave a residue which was taken in 2% HCl and concentrated to dryness. The resulting residue was then crystallized from 1:1 pyridine: 95% ethanol to give the desired product. mp 162° C. (dec), IR (KBr): 1960 cm$^{-1}$ (C=C=C), $^1$H NMR: (delta D$_2$O): 1.9 (m, 4H, CH$_2$), 3.05 (t, 2H, CH$_2$), 5.2 (d, 2H, CH$_2$=C), 5.6 ppm (dd, 1H, HC=C), $^{13}$C NMR: (delta D$_2$O): 208.9 ppm (C=$\underline{C}$=C), MH+171.

EXAMPLE 22

2-Amino-2-(imidazol-4-ylmethyl)penta-3,4-dienoic acid dihydrochloride 3 g of 2-(benzoylamino)-2-(imidazol-4-ylmethyl)-penta-3,4-dienoic acid was dissolved in 50 ml of 20% hydrochloric acid and heated to 80° C. for 2 to 3 days. On cooling, the reaction mixture was applied to an ion-exchange column and eluted with water and then 20% pyridine-water. The amino acid containing fractions were pooled and concentrated to give a residue. The desired material was further purified by HPLC RP-18 (5% MeOH-water, pH 4.5 acetate-citrate (2:1) buffer) and finally as the hydrochloride salt. Alternatively, the free amino acid was obtained by crystallization from acetone/water after acidic hydrolysis, gradient ion-exchange chromatography and desalting.

The title compound has the following physical properties: mp 205°-235° C. (dec), IR (KBr); 1977 cm$^{-1}$ (C=C=C) $^1$HNMR; (delta D$_2$O); 3.5 (AB, 2H, CH$_2$—), 5.25 (d, 2H, CH=C), 5.7 (d, 1H, HC=C), 7.45 (s, 1H, im-CH), 8.75 ppm (s, 1H, im-CH), $^{13}$NMR; (delta D$_2$O); 209.0 ppm (C=$\underline{C}$=C), MH+194.

EXAMPLE 23

2-Amino-3-methyl-3,4-pentadienoic acid

To an LDA solution (75.6 mmole prepared from diisopropylamine and 1.55M n-butyl lithium at −78° C.) in 100 ml of dry THF was added dropwise 36 mmole of N-BOC-glycine butynal ester (prepared from N-BOC-glycine and 2-butyn-1-ol according to the method of R. Olsen, et al, JOC, 47, 1962, 1982), in 20 ml of THF. After 1 hour, 9.6 ml of chlorotrimethylsilane was added and the reaction mixture was slowly brought to room temperature and then heated to reflux for 1 hour. On cooling to room temperature, 20 ml of methanol was added and after another hour the reaction mixture was concentrated. The resulting residue was taken in ethyl acetate and extracted repeatedly with 5% NaHCO$_3$. The aqueous portion was acidified in a two phase system containing CH$_2$Cl$_2$ with 20% HCl to pH 3.0. The CH$_2$Cl$_2$ portion was separated and the aqueous phase repeatedly extracted with CH$_2$Cl$_2$. The combined CH$_2$Cl$_2$ extracts were washed once with water, brine and dried over anhydrous MgSO$_4$. On concentration 1.3 gm of a residue showing an allene band at 1960 cm$^{-1}$ was obtained. This was taken in 50 ml of a saturated HCl ethyl acetate solution at room temperature upon which a yellow precipitate formed. After 1 hour, the reaction mixture was concentrated and the resulting residue taken in water and washed with CH$_2$Cl$_2$. The aqueous portion was then applied on an ion-exchange column (H+) eluting with 20% pyridine-water. The eluant was concentrated, partially purified by reverse phase chromatography and upon crystallization from acetone-water, the desired product was obtained: mp. 195°-200° C. (dec), IR (KBr): 1960 cm$^{-1}$ (C=C=C), $^1$H NMR (δD$_2$O): 1.82 (t, 3H, J=3.2 Hz, CH$_3$), 4.2 (t, 1H, J=1.7 Hz, CHN), 5.0 ppm (m, 2H, H$_2$C=C).

In the same manner, 2-amino-3,4-pentadienoic acid was obtained from N-BOC-glycine 3-trimethylsilyl-2-propynyl ester. After the [3.3] rearrangement of the ester, the trimethylsilyl group was removed by treatment with 0.1N NaOH/MeOH for 2 hours at room temperature. Ater removing the BOC group with HCl/EtOAc, ion-exchange chromatography and HPLC reverse phase chromatography, the desired product was obtained: $^1$H NMR (δD$_2$O): 4.25 (m, 1H, CHN), 5.15 (m, 2H, H$_2$C=C), 5.5 ppm (app t, J=6.7 Hz, HC=C).

EXAMPLE 24

In Vitro Testing

Compounds of this invention inactivate α-amino acid decarboxylase enzymes. The following exemplifies procedures employed to characterize the inactivation properties of these compounds.

Assay Procedures

Mammalian DOPA decarboxylase was isolated and purified from porcine kidney by the procedure of Borri-Voltatorni et al [Eur. J. Biochem., 93, 181 (1979)] with modifications as introduced by Rudd and Thanassi [Biochemistry, 20, 7469 (1981)]. Bacterial L-phenylalanine and L-tyrosine decarboxylases ex *Streptococcus faecallis* were purchased from Sigma Chemical Co. as crude extracts and studied without further purification.

Time dependent inactivation of mammalian DOPA decarboxylase was monitored by incubation of enzyme with 4 to 100 molar equivalent excess of 2-amino-2-(3,4- dihydroxybenzyl)penta-3,4-dienoic acid at pH 6.8 and 37° C. At appropriate time intervals, aliquots of the mixture were withdrawn, diluted 30-fold into excess L-DOPA (2 mM) and residual DOPA decarboxylase activity determined.

DOPA decarboxylase activity was routinely measured by liquid chromatography and electrochemical detection of catecholamine products. DOPA decarboxylase (1-5 micrograms, 1-20 units) was incubated with L-DOPA (2000 micromolar, 150 microliters) and PLP (10 micromolar) in 0.1M phosphate at pH 6.8 and 37° C. After 1-10 minutes, the reaction was quenched with citric acid (2M, 25 microliters), diluted two-fold with distilled water and 10 microliter aliquots were analyzed by HPLC on a reverse phase Brownlee RP-18 column. Isocratic elution with pH 4.35 buffer [0.1M NaOAc (63% v/v), 0.1M citric acid (32% v/v) and methanol (15% v/v)] at a flow rate of 2.5 ml/min. afforded baseline resolution of dopamine (RT=2.8 min.) from L-DOPA (RT=1.9 min.).

Quantification of dopamine was accomplished by preoxidation of the catechol to the ortho quinone at +0.25 volts in the first analytical electrochemical cell, followed by the selective reduction of ortho quinone in the second analytical cell set at −0.25 volts. This configuration for the ESA electrochemical detector allowed highly sensitive and selective detection of catecholamines (less than 10 picomoles/injection).

The time dependent inactivation of bacterial aromatic amino acid decarboxylases with 200-1000 micromolar inhibitor, e.g. 2-amino-2-(4-hydroxybenzyl)-penta-3,4-dienoic acid or 2-amino-2-benzylpenta-3,4-dienoic acid, was monitored at pH 5.5 and 37° C. Residual activity of tyrosine decarboxylase ex *Streptococcus faecallis* was determined by measurement of p-tyramine production at pH 5.5 and 37° C. p-Tyramine was separated by HPLC and quantified by electrochemical oxidation at +0.7 volts.

Residual activity of L-phenylalanine decarboxylase ex *Streptococcus faecallis* with L-phenylalanine (2 mM) as substrate was meaasured by gas chromatographic analysis of phenylethylamine production. Direct injection of enzymatic reaction mixture (1-5 microliters) onto a standard glass column packed with 10% Apiezon L on Chromosorb 80/100 deactivated with 2% KOH allowed separation of aromatic amine from the reaction mixture. FID detection quantified the rate of product formation.

EXAMPLE 25

In Vivo Testing

Methods

Male Sim:(S.D.)fBR rats weighing 180-335 g were used for these experiments. Groups of 5 rats were individually housed and received water, or various doses of either 2-amino-2-(3-hydroxybenzyl)penta-3,4-dienoic acid or 2-amino-2-(3,4-dihydroxybenzyl)penta-3,4-dienoic acid 30 l minutes before 200 mg/kg of L-DOPA, i.p. Beginning 15 minutes later, behavioral observations were made at 15 minutes intervals for 2 hours. Behavoir was scored as follows:

0=Sleeping
1=Awake and quiet
2=Alert and moving
3=Alert with intermittent sniffing
4=Continuous sniffing
5=Intermittent gnawing
6=Continuous gnawing Results 2-Amino-2-(3-hydroxybenzyl)penta-3,4-dienoic acid at 3-30 mg/kg, i.p. or 30-150 mg/kg, s.c. potentiated the behaviors induced by L-DOPA. Likewise, 2-amino-2-(3,4-dihydroxybenzyl)penta-3,4-dienoic acid was active at 30 mg/kg, i.p. or s.c.

TABLE 1

| Compound | Dose mg/kg | Route | Mean Behavior Score at 60 min. |
| --- | --- | --- | --- |
| Water | — | i.p. | 1.0 |
| 2-amino-2-(3-hydroxybenzyl)-penta-3,4-dienoic acid | 30-150 | s.c. | 3.4 |
|  | 3-30 | i.p. | 3.4 |
| 2-amino-2-(3,4-dihydroxybenzyl)-penta-3,4-dienoic acid | 30 | s.c. | 4.0 |
|  | 30 | i.p. | 4.0 |

EXAMPLE 26

Toxicity of 2-Amino-2-(3-hydroxybenzyl)penta-3,4-dienoic acid 2-amino-2-(3-hydroxybenzyl)penta-3,4-dienoic acid prepared in CMC vehicle was administered once daily to groups of 6 male mice at doses 0, 62.5, 125, 250, and 500 mg/kg. The animals were observed for 21 days and no deaths were noted in any of the dose groups. Therefore, the $LD_{50}$ (acute, oral, mouse) for 2-amino-2-(3-hydroxybenzyl)penta-3,4-dienoic acid is greater than 500 mg/kg.

Other compounds of this invention also do not exhibit toxicity at similar dose levels.

What is claimed is:

1. A compound of the formula

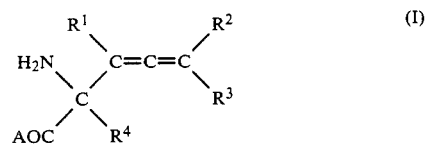

or a pharmaceutically acceptable salt thereof wherein:

$R^1$, $R^2$ and $R^3$ are selected from the group consisting of: hydrogen; alkyl of 1 to 6 carbon atoms; trifluoromethyl; phenyl; and phenylalkyl of 7 to 9 carbons where the ring is substituted with halo, halo alkyl of 1 to 6 carbon atoms, alkyl of 1 to 6 carbon atoms, hydroxy, alkoxy of 1 to 6 carbon atoms or amino; wherein at least two of $R^1$, $R^2$ and $R^3$ are hydrogen or alkyl; and wherein at lest one of $R^2$ and $R^3$ is hydrogen when $R^4$ is hydrogen;

$R^4$ is selected from the group consisting of: hydrogen; alkyl of 1 to 6 carbon atoms; —(CHR)$_m$XR' wherein m is 1 or 2 and X is oxygen or sulfur and R and R' are independently hydrogen or methyl; —(CH$_2$)$_n$—COY wherein n is 1 or 2 and Y is hydroxy or amino; —(CH$_2$)$_o$NHC(NH$_2$)(NH) wherein o is 2, 3 or 4; —(CH$_2$)$_p$—NH$_2$ wherein p is 2, 3, 4 or 5; a radical of the formula

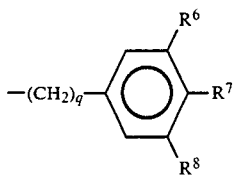

wherein q is 1 or 2 and $R^6$, $R^7$ and $R^8$ are independently hydrogen or hydroxy; and a radical of the formula

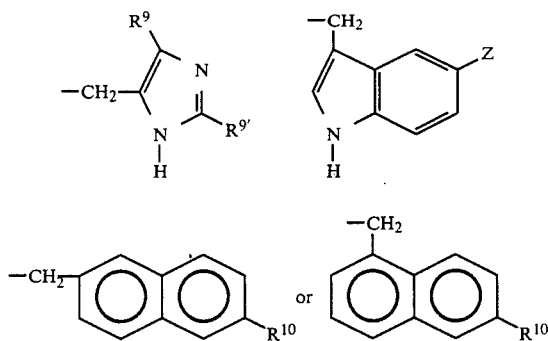

wherein $R^9$ and $R^{9'}$ are independently hydrogen or trifluoromethyl, $R^{10}$ is hydrogen, hydroxy or methoxy, and Z is hydrogen or hydroxy; and A is selected from the group consisting of: —OH; —OS wherein S is a cationic portion of a pharmaceutically acceptable salt; —OE wherein E is alkyl of 1 to 22 carbon atoms or arylalkyl of 7 to 10 carbon atoms; amino; mono-alkylamino wherein the alkyl radical has 1 to 6 carbon atoms; and di-alkyl amino wherein the alkyl radicals have 1 to 6 carbon atoms.

2. A compound according to claim 1 wherein:

$R^1$, $R^2$ and $R^3$ are independently selected from the group consisting of: hydrogen, methyl, ethyl, trifluoromethyl and benzyl; and $R^4$ is selected from the group consisting of: hydrogen; methyl; —(CH$_2$)$_3$—NH$_2$; —(CH$_2$)$_4$NH$_2$; —(CH$_2$)$_2$—COY, wherein Y is hydroxy or amino; a radical of the formula

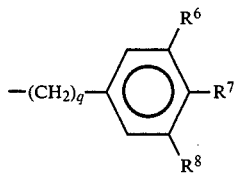

where q is 1 or 2 and $R^6$, $R^7$ and $R^8$ are independently hydrogen or hydroxy; and a radical of the formula

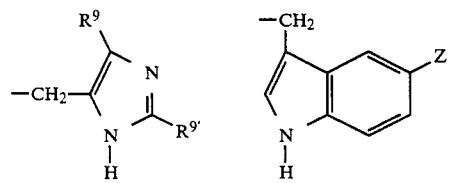

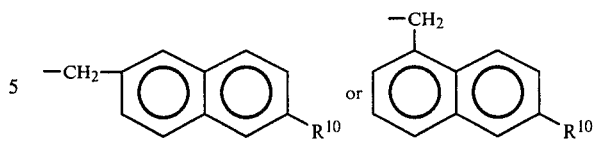

wherein $R^9$ and $R^{9'}$ independently hydrogen, alkyl of 1 to 4 carbons, halo or CF$_3$, $R^{10}$ is hydrogen, hydroxy or methoxy and Z is hydrogen or hydroxy.

3. A compound according to claim 2 wherein $R^1$, $R^2$ and $R^3$ are hydrogen.

4. The compound of claim 3 which is 2-amino-2-(imidazol-4-ylmethyl)penta-3,4-dienoic acid or a pharmaceutically acceptable salt thereof.

5. The compound of claim 3 which is 2-amino-2-(2-carboxyethyl)penta-3,4-dienoic acid or a pharmaceutically acceptable salt thereof.

6. The compound of claim 3 which is 2-amino-2-(3-amino-n-propyl)penta-3,4-dienoic acid or a pharmaceutically acceptable salt thereof.

7. The compound of claim 3 which is 2-amino-2-(4-hydroxybenzyl)penta-3,4-dienoic acid or a pharmaceutically acceptable salt thereof.

8. The compound of claim 3 which is 2-amino-2-(3-hydroxybenzyl)penta-3,4-dienoic acid or a pharmaceutically acceptable salt thereof.

9. The compound of claim 3 which is 2-amino-2-(3,4-dihydroxybenzyl)penta-3,4-dienoic acid or a pharmaceutically acceptable salt thereof.

10. The compound of claim 3 which is 2-aminopenta-3,4-dienoic acid or a pharmaceutically acceptable salt thereof.

11. The compound of claim 3 which is 2-amino-2-benzylpenta-3,4-dienoic acid or a pharmaceutically acceptable salt thereof.

12. The compound of claim 3 which is 2-amino-2-($\beta$-naphthylmethyl)-penta-3,4-dienoic acid or a pharmaceutically acceptable salt thereof.

13. The compound of claim 2 wherein $R^1$ is methyl, and $R^2$ and $R^3$ are hydrogen.

14. The compound of claim 13 which is 2-amino-2-benzyl-3-methylpenta-3,4-dienoic acid or a pharmaceutically acceptable salt thereof.

15. The compound of claim 13 which is 2-amino-3-methylpenta-3,4-dienoic acid or a pharmaceutically acceptable salt thereof.

16. The compound of claim 2 wherein $R^1$ is hydrogen, and $R^2$ and $R^3$ are independently hydrogen or methyl or a pharmaceutically acceptable salt thereof.

17. The compound of claim 16 which is 2-amino-2-benzylhexa-3,4-dienoic acid or a pharmaceutically acceptable salt thereof.

18. The compound of claim 16 which is 2-amino-2-(3-hydroxybenzyl)hexa-3,4-dienoic acid or a pharmaceutically acceptable salt thereof.

19. A compound selected from the group consisting of:

2-amino-3-methylpenta-3,4-dienoic acid;
2-amino-2-(imidazol-4-ylmethyl)penta-3,4-dienoic acid;
2-amino-2-(2-carboxyethyl)penta-3,4-dienoic acid;
2-amino-2-(3-amino-n-propyl)penta-3,4-dienoic acid;
2-amino-2-(3-hydroxybenzyl)penta-3,4-dienoic acid;
2-amino-2-(4-hydroxybenzyl)penta-3,4-dienoic acid;
2-amino-2-(3,4-dihydroxybenzyl)penta-3,4-dienoic acid;

2-amino-2-(β-naphthylmethyl)-penta-3,4-dienoic acid;
2-amino-2-benzyl-3-methylpenta-3,4-dienoic acid;
2-aminopenta-3,4-dienoic acid;
2-amino-2-(3-hydroxybenzyl)penta-3,4-dienoic acid;
2-amino-2-(3,4-dihydroxybenzyl)penta-3,4-dienoic acid;
2-amino-2-benzylpenta-3,4-dienoic acid;
2-amino-2-(4-amino-n-butyl)penta-3,4-dienoic acid;
2-amino-2-methylpenta-3,4-dienoic acid;
2-amino-2-(5-hydroxyindol-3-yl methyl)penta-3,4-dienoic acid;
2-amino-2-(3-hydroxybenzyl)hexa-3,4-dienoic acid;
2-amino-2-benzylhexa-3,4-dienoic acid; and
2-amino-2-(3-amino-n-propyl)penta-3,4-dienoic acid.

20. The compound of claim 19 which is 2-amino-2-(3-hydroxybenzyl)penta-3,4-dienoic acid.

21. The compound of claim 19 which is 2-amino-2-(3,4-dihydroxybenzyl)penta-3,4-dienoic acid.

22. The compound of claim 19 which is 2-amino-2-(4-amino-n-butyl)penta-3,4-dienoic acid.

23. The compound of claim 19 which is 2-amino-2-methylpenta-3,4-dienoic acid.

24. The compound of claim 19 which is 2-amino-2-(5-hydroxyindol-3-ylmethyl)penta-3,4-dienoic acid.

25. The compound of claim 19 which is 2-amino-2-(3-amino-n-propyl)penta-3,4-dienoic acid.

26. A pharmaceutical composition for treating a disease state associated with decarboxylase enzyme activity, comprising a therapeutically effective amount of a compound according to claim 1 in admixture with a pharmaceutically acceptable excipient.

27. A method for inhibiting amino acid decarboxylase enzyme activity which method comprises administering a therapeutically effective amount of a compound according to claim 1 to a mammal.

28. A method for treating a fungal infection in a mammal, said method comprising administering a therapeutically effective amount of a compound of claim 1, wherein $R^2$, $R^3$ and $R^4$ are hydrogen, to the mammal.

29. The method of claim 28 wherein the compound is 2-amino-3-methyl-penta-3,4-dienoic acid or a pharmaceutically acceptable salt thereof.

* * * * *